United States Patent [19]

Blackshear, Jr. et al.

[11] Patent Number: 5,308,356
[45] Date of Patent: May 3, 1994

[54] PASSIVE PERFUSION ANGIOPLASTY CATHETER

[76] Inventors: Perry L. Blackshear, Jr., 29 Birchwood Rd., Mahtomedi, Minn. 55115; Joseph L. Blackshear, 700 Ranch Rd., Ponte Vedra Beach, Fla. 32082

[21] Appl. No.: 22,573

[22] Filed: Feb. 25, 1993

[51] Int. Cl.$^5$ ............................................ A61M 29/00
[52] U.S. Cl. ...................................... 606/194; 604/96
[58] Field of Search ....................... 606/191, 194, 195; 604/96-101; 128/207.15

[56] References Cited

U.S. PATENT DOCUMENTS

| | | |
|---|---|---|
| 4,484,579 | 11/1984 | Meno et al. ........................ 606/194 |
| 4,498,473 | 2/1985 | Gereg . |
| 4,581,017 | 4/1986 | Sohata . |
| 4,681,564 | 7/1987 | Landreneau . |
| 4,737,147 | 4/1988 | Ferrando . |
| 4,737,388 | 11/1988 | Hofmann . |
| 4,762,130 | 8/1988 | Fogarty . |
| 4,777,951 | 10/1988 | Cribier . |
| 4,881,939 | 11/1989 | Newman . |
| 4,934,786 | 6/1990 | Krauter . |
| 4,950,232 | 8/1990 | Ruzicka . |
| 5,147,377 | 9/1992 | Sahota ................................. 604/96 |

OTHER PUBLICATIONS

Avedissian et al, Percutaneous Transluminal Coronary Angioplasty, Catheterization Curriculum, 1989.
Chin et al, Balloons and Mechanical Devices, Year Book Medical Publishers, Inc., pp. 217–227.
Fogarty et al, Adjunctive Intraoperative Arterial Dilation, Arch Surgery vol. 116, Nov. 1981 pp. 1391–1397.
Chin et al, Long-term Results of Introoperative Balloon Dilatation, Cardiovasc. Surg., 1989, pp. 454–458.

Primary Examiner—Stephen C. Pellegrino
Assistant Examiner—William Lewis
Attorney, Agent, or Firm—Cushman, Darby & Cushman

[57] ABSTRACT

A passive perfusion angioplasty catheter is provided which includes an elongated flexible member defining an inflation lumen and an inflatable balloon member affixed to a distal end of the flexible member for pressing against an interior wall of an artery. The balloon member defines at least one passage between a surface thereof and the interior wall permitting blood to flow therethrough when the balloon member is pressed against the interior wall. A method of percutaneous transluminal angioplasty is also provided.

56 Claims, 9 Drawing Sheets

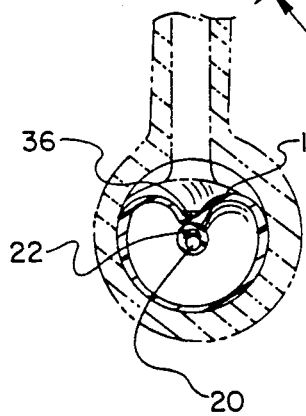
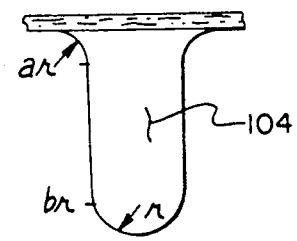
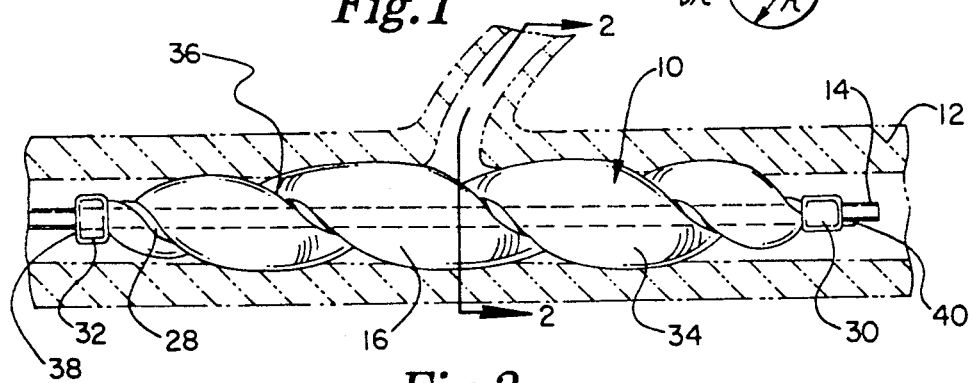
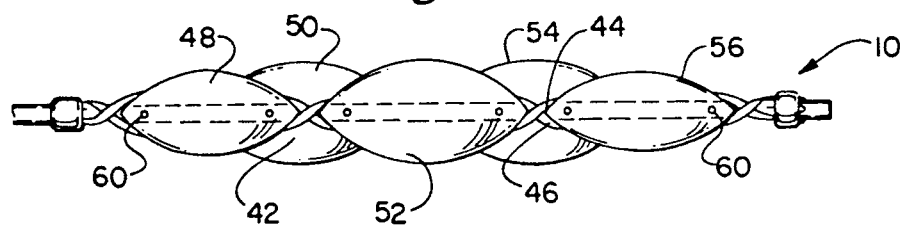

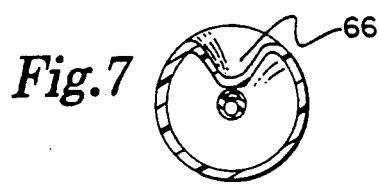
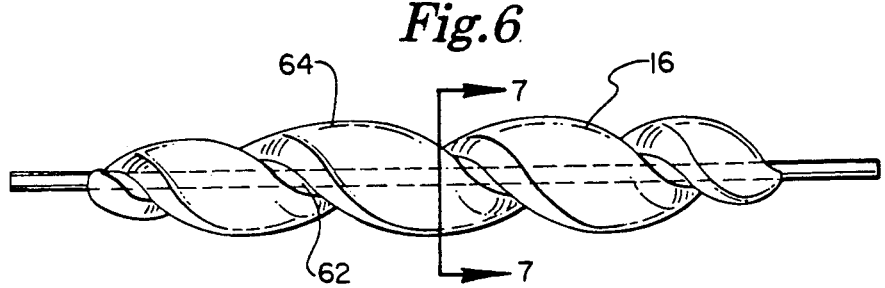
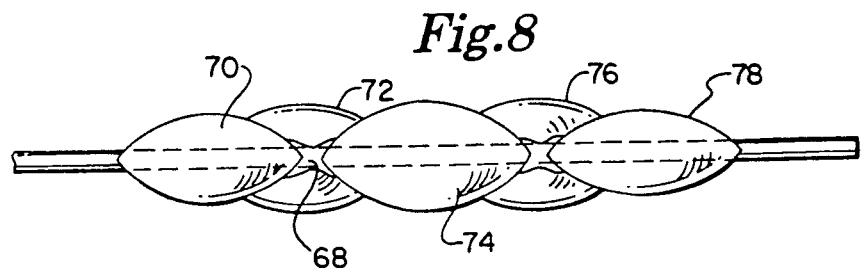
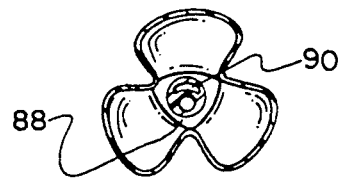
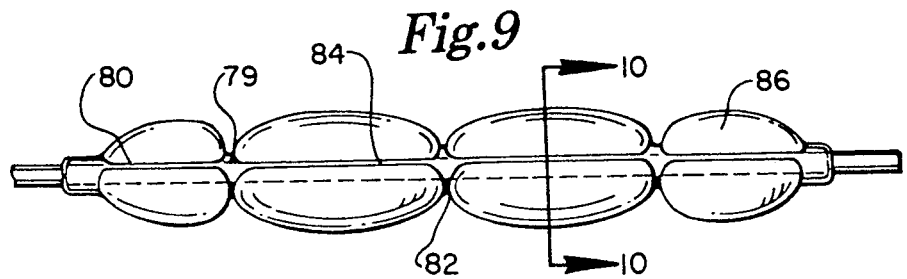

PASSIVE PERFUSION ANGIOPLASTY CATHETER

BACKGROUND OF THE INVENTION

1. Field of the Invention

This invention relates generally to the field of angioplasty, the balloon-catheter reconstruction of a blood vessel. In particular, it relates to a unique passive perfusion balloon catheter for use in percutaneous transluminal angioplasty, which allows blood to flow through the artery between the arterial wall and the irregular surface of the balloon to the distal side of the stenosis during dilation of the blood vessel.

2. Description of the Related Art

Atherosclerosis is a debilitating disease that is characterized by irregularly distributed lipid deposits, called plaque, on and within the walls of arteries. Ultimately, atherosclerosis results in a narrowing of, and a total or partial occlusion of blood flow through, the arterial lumen. Atherosclerosis typically begins in the second or third decade of life and usually affects arteries throughout the vascular system in varying degrees.

In some portions of an affected artery, the build up of plaque results in a more severe narrowing called a "stenosis." If the stenosis is severe, blood flow is restricted or precluded and surgical or balloon catheter treatment is often necessary on clinical grounds to restore patency to the area. When stenosis is found over 70-80 % of a coronary artery, myocardial ischemia (the inadequate flow of oxygen rich blood to the myocardium, the muscle layer of the heart) can occur. Myocardial ischemia is sometimes accompanied by angina pectoris, a constricting pain in the chest, shoulder or arms. Also attendant with the progression of atherosclerosis are coronary artery spasm and the formation of life-threatening intraluminal thrombi, commonly referred to as blood clots.

Percutaneous transluminal angioplasty, using a balloon catheter, was first introduced in the mid-1970's and has become a widely accepted method for treating obstructed arteries. There are currently four basic designs employed in percutaneous transluminal angioplasty 1) standard balloon over a wire; 2) low profile, small shaft balloon over a wire; 3) standard shaft balloons with fixed or partially movable wires and 4) balloon on a wire system. The procedure will be described applying the first design.

The procedure is typically performed by first making a puncture wound in the patient's right groin to gain access to the right femoral artery. A guide wire is passed through the artery and advanced through the arterial system until the distal end of the wire reaches the arterial stenosis, whether iliac, femoropopliteal, aortic, renal, splanchnic, or brachiocephalic. For many stenosis, in particular those in coronary arteries, a guiding catheter is advanced over the guide wire until its distal end passes over the distal end of the guide wire. The guide wire is then removed and a special PTA (percutaneous transluminal angioplasty) wire is advanced through the guiding catheter up to the locus of the stenotic lesion. The physician then manipulates the proximal end of the PTA wire to pass it through the stenotic lesion that is obstructing the artery. Once the PTA wire passes successfully through the stenotic lesion, a PTA balloon angioplasty catheter is passed over the PTA wire by feeding the distal end of the balloon catheter over the proximal end of the wire and then pushing the balloon catheter over the wire until the balloon is adjacent to (within) the stenotic lesion. Thus positioned, the balloon is inflated by injecting thereinto a bio-compatible fluid, such as saline. As the balloon inflates, it stretches the artery wall, distorts the plaque defining (or forming) the stenotic lesion and frequently produces a tear in the inner layers of the vessel wall. The plaque is displaced thus improving or restoring patency to the target artery.

Conventional angioplasty catheters have the undesirable effect of completely denuding the intimal surface, the innermost layer of endothelial cells lining the artery, when the balloon surface contacts the intima. An intact endothelial surface prevents contact between platelets and other components of the intima which act as powerful agonists of platelet adhesion and activation. If the depth of arterial injury is extensive, a powerful stimulation of the clotting system may occur leading to thrombosis and occlusion. Limiting the extensive the loss of endothelial cells may protect against thrombosis. Thrombi which form in the arterial lumen can block blood flow despite a physician's successful efforts in displacing the plaque. One method of treating this problem has been the use of prolonged inflation periods. However, longer inflation times are only practical (can only be utilized) if the catheter allows blood to continue to flow through the artery.

Conventional angioplasty catheters used to perform percutaneous transluminal angioplasty also have the disadvantage of completely occluding blood flow while the balloon is expanded in the artery. This can cause damage to the arterial wall by preventing the endothelial and smooth muscle cells from absorbing oxygen and, if the stenosis is in a coronary artery, may cause serious damage to those portions of the heart that receive blood via that artery. Consequently, angioplasty is not only a painstaking task for the physician who must inflate the balloon for only a few seconds and then deflate the balloon to allow blood to continue to flow through the artery, but is also potentially dangerous for the patient. Indeed, if the balloon is inflated for longer than 60-90 seconds, the patient may experience severe angina. shock, and/or rhythm disturbances of the heart.

Angioplasty procedures currently being used in practice also result in a re-stenosis rate of 20-50%.

Attempts to overcome these problems have been met with limited success. For example, a passive perfusion-type balloon catheter has been developed which has blood entry side hole(s) proximal to the balloon and blood exit hole(s) distal to the balloon. The side holes permit blood to pass through the lumen of the catheter, by-passing the balloon and stenosis as the inflated balloon blocks the arterial lumen. However, typically such catheters have a large profile, even with the balloon deflated, because the main body of the catheter must be relatively large to allow the blood to flow therethrough, and are relatively stiff. These characteristics limit their usefulness as the primary catheter for very tightly stenosed arteries, small vessels or tortuous coronary arteries. Furthermore, although blood may flow straight through to the distal end of the stenosed region, the inflated balloon still occludes side branches and, therefore, does not protect the myocardium served by such side branching arteries from ischemia.

Additionally, the intimal surface which comes in contact with the inflated balloon is still completely denuded, making the subsequent formation of thrombi or restenosis more likely. Even further, since flow rates are proportional to arterial pressure in any passive perfusion system, patients with hypotension may not obtain relief of myocardial ischemia with the limited passive autoperfusion that conventional catheters allow.

SUMMARY OF THE INVENTION

It is an object of the method of percutaneous transluminal angioplasty and passive perfusion balloon catheter provided in accordance with the present invention to solve the problems outlined above that have heretofore inhibited successful percutaneous transluminal angioplasty. More particularly, the invention herein described is a modification of the existing coronary angioplasty balloon to permit a more generous blood flow to areas of the artery distal to the inflated balloon, permit autoperfusion of smaller vessels, tortuous vessels and lesions involving side branching arteries, provide a shorter diffusion path for oxygen delivery to the vessel walls at the occlusion site, and limit denudation of the intima. The balloon and catheter in accordance with the present invention includes an elongated flexible member defining an inflation lumen and inflatable balloon means affixed to a distal end of the flexible member for pressing against an interior wall of an artery. The balloon means defines at least one passage between a surface thereof and the interior wall permitting blood to flow therethrough when the balloon means is pressed against the interior wall.

Percutaneous transluminal angioplasty in accordance with the present invention includes the steps of providing a catheter having an elongated flexible member defining an inflation lumen and inflatable balloon means affixed to a distal end of said flexible member for pressing against an interior wall of an artery, the balloon means defining at least one passage between a surface thereof and the interior wall; inserting the catheter into an artery so that the balloon means is disposed at point were blood flow is restricted; inflating and expanding the balloon means so that the balloon means presses against the interior wall to reduce a restriction in the artery; and permitting blood to flow in the at least one passage so as to pass between the balloon means and the interior wall.

One of the advantages of the present invention is that prolonged low pressure dilation of arteries (in which dissection or thrombosis has complicated an otherwise routine angioplasty procedure) is now possible. Another advantage of the present invention is that the problems of myocardial ischemia, angina, and the potential for circulatory collapse are substantially reduced or eliminated. Perhaps, most significantly, the present invention allows side branch perfusion, improves oxygenation of the arterial wall and retains portions of surface endothelium to facilitate an enhanced re-endothelialization.

BRIEF DESCRIPTION OF THE DRAWINGS

FIG. 1 is a broken away side elevational view of the passive perfusion balloon angioplasty catheter in accordance with the present invention during a percutaneous transluminal angioplasty procedure;

FIG. 2 is a cross-sectional view taken along line 2—2 of FIG. 1;

FIG. 3 is a side elevational view of a second embodiment of a balloon tip for a catheter in accordance with the present invention;

FIG. 4 is a schematic cross-sectional view depicting an unstable groove shape;

FIG. 5 is an enlarged cross-sectional view of the optimum angle of the grooved wall of the blister in accordance with the invention;

FIG. 6 is a side elevational view of a third embodiment of a balloon tip for a catheter in accordance with the present invention;

FIG. 7 is a cross-sectional view taken along line 7—7 of FIG. 6;

FIG. 8 is a side elevational view of a fourth embodiment of a balloon tip for a catheter in accordance with the present invention;

FIG. 9 is a side elevational view of a fifth embodiment of a balloon tip for a catheter in accordance with the present invention;

FIG. 10 is a cross-sectional view taken along line 10—10 of FIG. 9;

FIG. 24b is an end view of the balloon shown in FIG. 24a;

DETAILED DESCRIPTION OF THE PRESENTLY PREFERRED EXEMPLARY EMBODIMENTS

Figure 13:
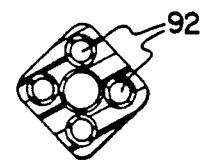
FIG. 13 is a cross-sectional view taken along line 13—13 of FIG. 11.

FIG. 1 depicts a first embodiment of a passive perfusion balloon catheter 10 in accordance with the present invention disposed within an artery 12. The balloon catheter 10 generally includes an elongated flexible cylinder or tubular member 14 and balloon member 16. Other details of the catheter structure proximal of the balloon, such as the proximal end configuration and radiopaque bands are not shown or described herein because a variety of such known features could be used in accordance with the invention and are not critical to the inventive balloon configurations.

The tubular member 14 or inflation tube defines a balloon inflation lumen 18 and a guide wire lumen 20. In the illustrated embodiment, the two lumens are separated by a lumen wall 22 that extends along the horizontal axis of the tubular member 14. The tubular member may be made from any number of high strength medical grade plastics, known for the manufacture of intravascular catheters including, by way of example, polyurethane, polyolefin, tetrafluoroethylene fluorocarbon polymer, polyethylene, nylon, or other suitable materials.

The balloon member 16 is made from polyvinyl chloride, polyethylene, polyethylene terephthalate (PET), polyolefin copolymer or other suitable medical grade materials which yield a strong non-compliant balloon capable of withstanding high inflation pressures. Balloon member 16 is thin-walled, having a thickness of about 0.001 to 0.010 cm but most preferably is 0.00254 cm thick. The length of balloon member may be varied depending on the configuration and location of the affected stenotic artery into which it is inserted.

For safety reasons, balloon material should exhibit limited strain under inflation. In some designs the external perfusion balloon requires strains as great as 400%. To accommodate strain requirement two alternate approaches are proposed: 1) Employ "S" shaped pleats in the relaxed surfaces which disappear under modest tension and 2) Employ elastomeric balloons with inelastic reinforcing which allows the strain but imposes limits. The detailed description below is limited to the first consideration.

Figure 21A:
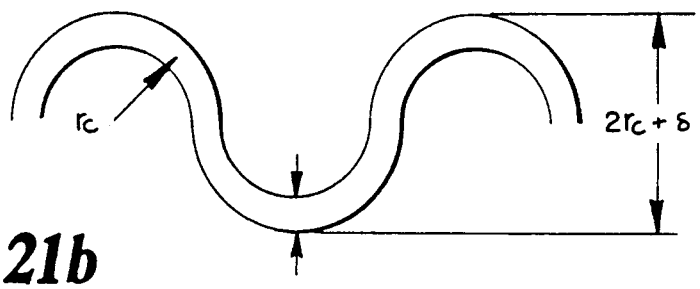
FIGS. 21a–21c are enlarged partial views of balloon pleats provided in accordance with the present invention.
Figure 21B:
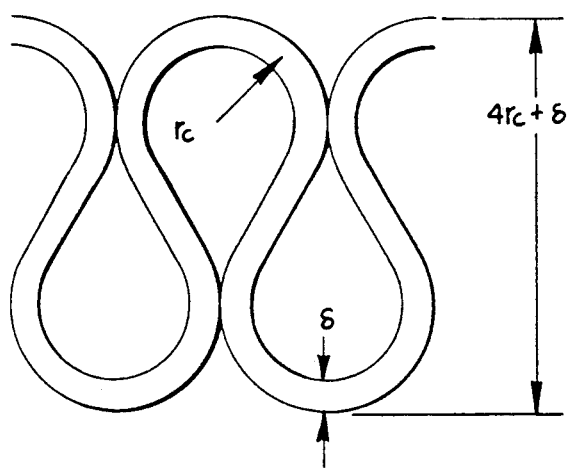
Figure 21C:
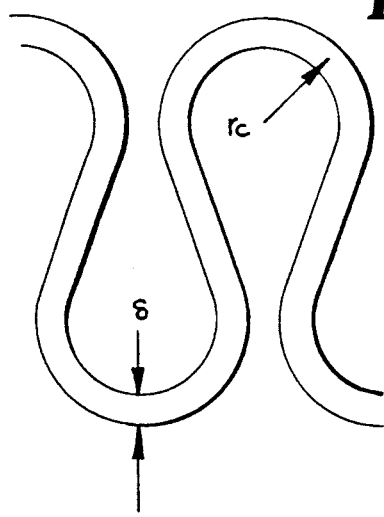
Figure 22:
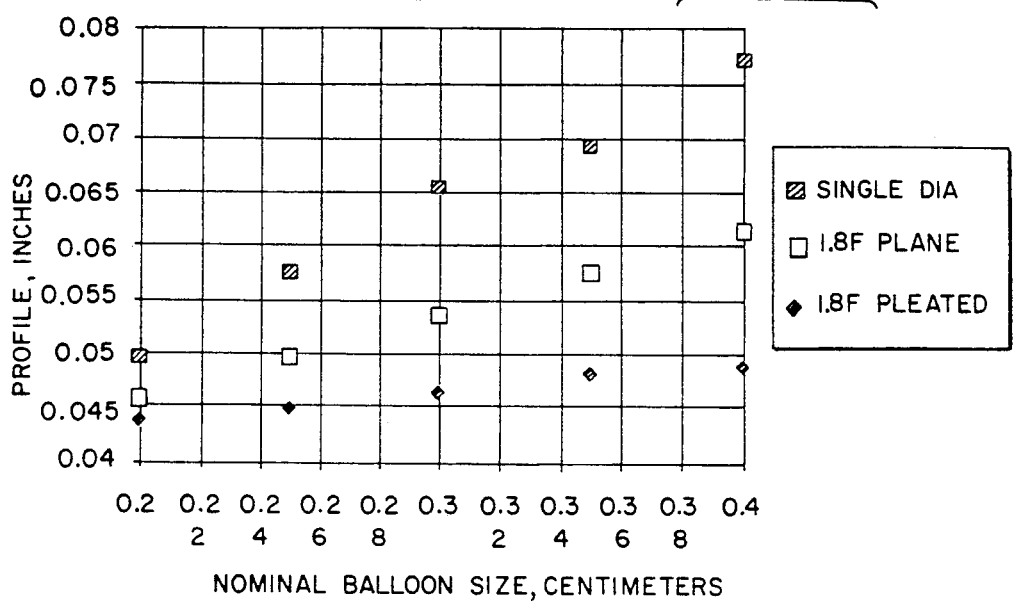
FIG. 22 is a graphical representation of balloon profile vs. balloon size in accordance with the present invention.
Figure 23A:
FIGS. 23a–23c are pleated balloon profiles provided in accordance with the present invention.
Figure 23B:
Figure 23C:
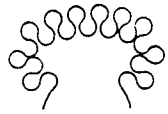

In the materials currently employed in balloons, strains as much as 10 to 20% with increased inflation pressures are not uncommon. These strains would tolerate pleats with radii of curvature of 5 to 2.5 times the thickness of the balloon material. Thus, if the balloon has a 0.001 inch thickness, pleats with radii of 0.005 to 0.0025 inches can be preformed in the material such that elongation in a single direction can be enhanced. Examples of such pleats are shown in FIGS. 21a–21c. FIG. 21a shows pleats consisting of a series of half circles of radius $r_c$. The resulting pleated membrane is $2r_c + \delta$ in thickness when the unpleated membrane is $\delta$. When these pleats are stretched so the membrane is straight, the length is approximately $\pi/2$ times the pleated length. The strain in the balloon is equal to $2\pi r_c/4r_c = \pi/2$. When the pleated membrane is shaped as depicted in FIG. 21b, the length ratio is $2\pi/1$, stretched/pleated and the thickness is $4r_c + \delta$. The configuration shown in FIG. 21c has a length ratio or 4.8 and a thickness of $4r_c + \delta$. Present balloon profiles in the deflated state range from a nominal 0.025 to 0.059 inches. These profiles represent the diameter of the portion of the balloon collapsed tightly around the guidewire or shaft. There is in addition, a flattened balloon "wing" extending to either side of the shaft. In the illustrated embodiment, these "wings" are not present. The profile is thus, also the size aperture that the balloon may enter. Three pleated deflated balloons profiles are shown in FIG. 22. These profiles have been calculated with the assumption that the $\delta = 0.001$ inches, $r_c = 2.5\ \delta$. The pleats have a thickness of $4r_c + \delta$ and provide a length ratio of 4.8. In the top curve in FIG. 22, the deflated balloon shows the same inner diameter about the entire circumference. In the middle curve, the valleys have a diameter 1.8 French ($\frac{1}{2}$ mm or 0.020 inches). The pleated surface has the diameter given as the profile and the two diameters are connected by a plane balloon surface. In the lower curve, the two diameters are connected by a pleated surface. In each case the profile is limited by the restriction that the pleats provide a length ratio of 4.8. FIGS. 23a–23c show these three cases calculated for a nominal 4 mm inflated balloon. FIG. 23a corresponds to the top curve in FIG. 22, FIG. 23b corresponds to the middle curve in FIG. 22, and FIG. 23c corresponds to the bottom curve on FIG. 22.

Figure 24B:
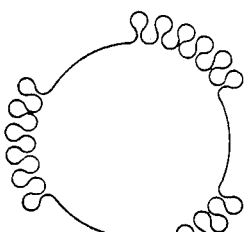
Figure 24A:
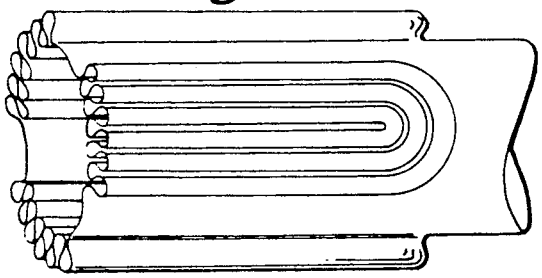
FIGS. 24a is a balloon showing pleat arrangements provided in accordance with the present invention.
Figures 24C, 24D:
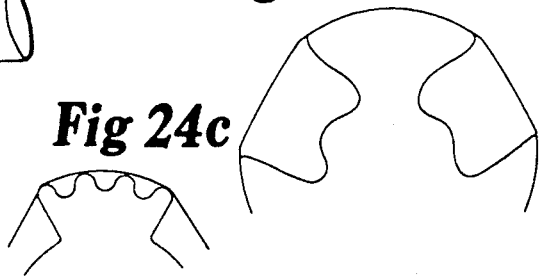
FIG. 24c is a partial view of the balloon in FIG. 24a partially inflated.
FIG. 24d is a partial view of the balloon in FIG. 24a fully inflated.

An example of the way the pleats are arrayed to provide the required strain is shown in FIGS. 24a–24d. Here, an increase in lobe perimeter of 420% is required as the lobes inflate. An increase of less than 20% in length is required. FIG. 24a shows how the deflated blister appears from above and FIG. 24b shows an end view. FIG. 24c shows the balloon partially inflated and FIG. 24d fully inflated in the confining artery.

Pleat design in the helix.

Figure 25:
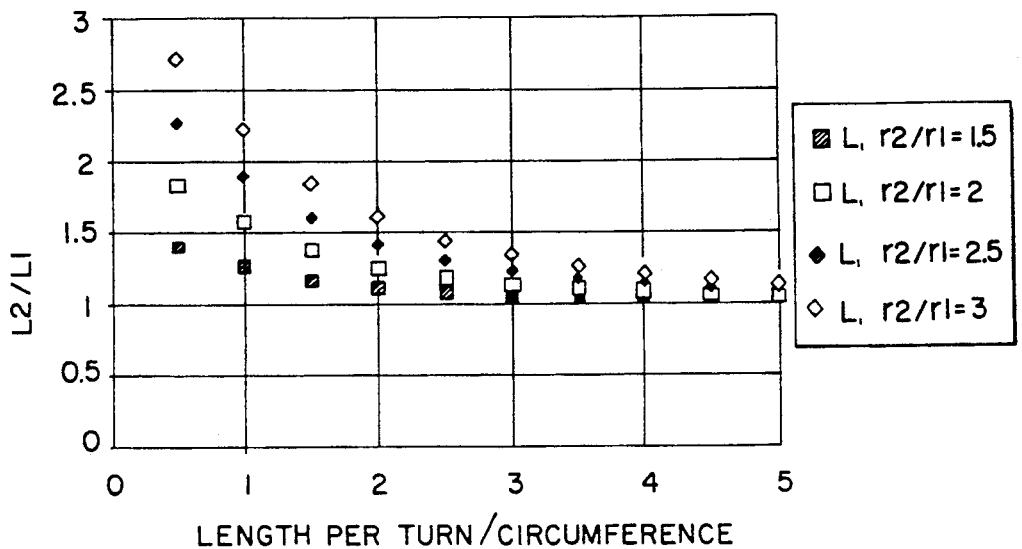
FIG. 25 is a graph showing the balloon length ratio as a function of the pitch of the helix.
Figure 26:
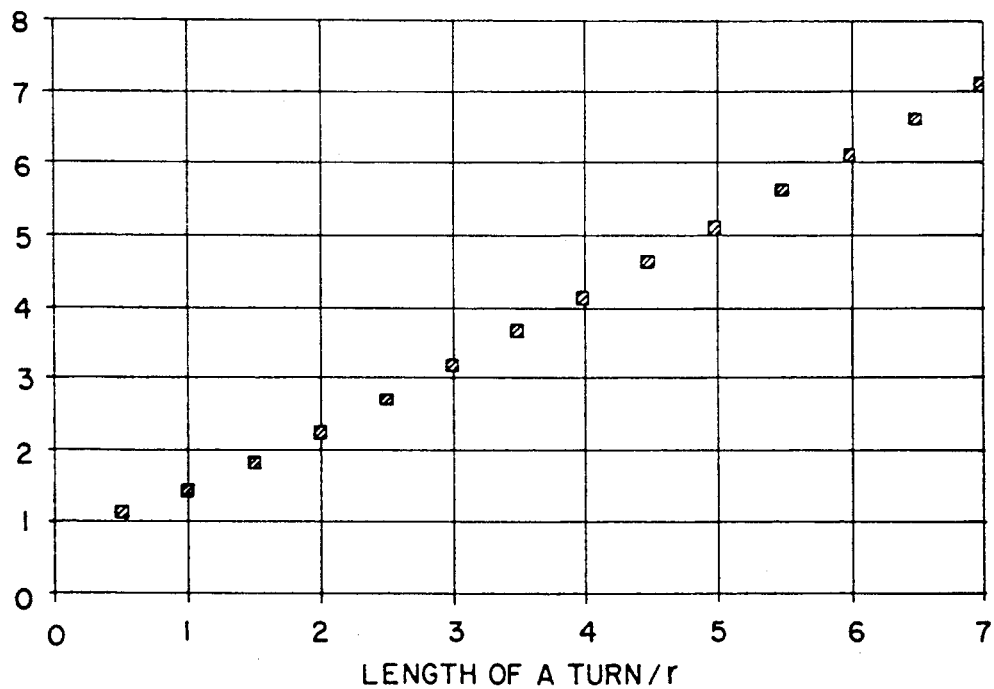
FIG. 26 is a graph showing the effect of increasing the pitch of the helix.

For blisters which wrap around the balloon axis, the distance along the crest of the blister will be longer when the balloon is inflated than when it is deflated. The length ratio is shown in FIG. 25 for different radii ratios as a function of the pitch of the helix. It can be seen that as the length per turn increases, the elongation becomes small enough to be accommodated by wrinkles at the blister ends. The price in reduced load bearing is reflected in an increase in the effective radius of curvature of the groove. This is shown in FIG. 26. It is seen that as the pitch increases, the radius of curvature approaches the product of pitch multiplied by $r_1$. In the embodiments described in the following paragraphs, the elastomeric behavior required to achieve the changes in shape during inflation is to be provided by these pleats which permit a balloon surface feature to exhibit 400 to 500% elongation while restricting the material strain to less than 10 to 20%.

Blowing the wrinkled, grooved balloons:

The present method of inflating a small tube in a heated mold lends itself readily to the fabrication of the wrinkled, grooved balloons of the invention. The mold is fabricated to form wrinkles opened to half their full extent. Suction, then, will produce the minimum profile with the wrinkles exhibiting a bending moment while full inflation will produce the open wrinkles, also under stress but with less strain than if the wrinkles had been blown in the collapsed configuration.

Stress consideration

In general, the balloon wall stress, $\sigma$, will be related to the pressure difference, $\Delta p$, the membrane thickness, $\delta$, and the radii of curvature of the surface, $r_1$ and $r_2$, by $$\sigma = \frac{\Delta p}{\sigma\left(\frac{1}{r_1} + \frac{1}{r_2}\right)}$$

except where the balloon is restrained by the artery wall in which case the above equation represents the upper limit.

In the helical designs considered here, $\sigma$ can be estimated by considering only the smaller of the two r's, especially since the larger will approach infinity, and will be represented as r' without subscript by $$\sigma = \frac{\Delta p r'}{\delta}$$

For the fully inflated balloon viewed in cross section there are two limiting radii, $r_i$, the innermost radius, ca 0.25 mm, and the outermost, $1 < r_o < 2$ mm. We define a local pitch of the helix, $$\frac{x r_i}{2 r_i r},$$

and can show that $$\frac{r'}{r_i} = \sqrt{\left(\frac{r}{r_i}\right)^2 + \left(\frac{x}{\pi 2 r_i}\right)^2}$$

Thus if

| $\frac{x}{2r_i} = 2$ | | |
| --- | --- | --- |
| $\frac{r}{r_i}$ | $\frac{r'}{r_i}$ | $\frac{r'}{r}$ |
| 1 | 1.38 | 1.38 |
| 2 | 2.22 | 1.11 |
| 3 | 3.14 | 1.05 |
| 4 | 4.11 | 1.03 |

Due to the blowing procedure by which the balloons are formed, the membrane thickness, $\delta$, will be thinnest where r and thus r' is greatest, the conditions limiting inflation pressures will be the load carrying ability of the outer wall of the blister or helix.

In accordance with the preferred embodiments, the balloon member 16 contains a single or multiple groove stabilized by a circumferential component of stress. In the embodiment of FIG. 1, the circumferential stress component is achieved by imposing a restraining helical shape, effected with a single helical band 28 and distal and proximal wraps 30, 32 respectively. The band 28 is helically wound around the outer surface 34 of the balloon member 16 and causes a groove 36 to form when balloon member is inflated. The groove 36 is disposed longitudinally along the entire length of balloon catheter 10. At the appropriate range of inflation pressure, 750 to 150 psi, the groove 36 becomes substantially recessed but is maintained open against the inflation pressure by virtue of circumferential components of wall tension, thus allowing the patient's blood to flow freely over and around balloon member 16.

The distal and proximal wraps 30, 32 are attached by force fitting, heat pressing or a suitable adhesive, and secure first and second ends 38, 40 of band 28 to the tubular member 14. The distal and proximal wraps 30, 32 may made from any elastomeric medical grade material such as polyethylene terephthalate or polyolefin copolymer.

FIG. 3 depicts a modified form or second embodiment of the present invention. As may be noted, the second embodiment is similar to the embodiment depicted in FIG. 1, and thus like elements are identified with like numbers.

In the embodiment of FIG. 3, a double helical groove 42 is formed by cross wrapping two bands 44, 46. Thus, one band 44 is wound helically clockwise around the longitudinal axis of balloon member 16 and the other band 46 is wound helically counter-clockwise around the longitudinal axis of balloon member 16. The bands cross at spaced locations on each side of the balloon member. When inflated, the helical configuration and points of cross over of bands 44, 46, cause the balloon member 16 to form blisters 48, 50, 52, 54, 56 with recessed grooves 42 therebetween. To that end, each balloon blister is inflated via respective inflation outlet port(s) 60 defined through the wall of the balloon inflation lumen of the tubular member 14 or through a single port via escapement grooves beneath the confining bands 44, 46. The recessed grooves 42 are maintained open against the inflation pressure by virtue of circumferential components of wall tension, thus allowing the patient's blood to flow freely around and between the blisters.

FIGS. 6 and 7 depict a modified form or third embodiment of the present invention. In accordance with this embodiment, the groove defining band 62 is an integral part of the balloon structure, which has a different inflation characteristic by virtue of having a different thickness or simply a different initial shape. Thus, the segment of the balloon member 16 which defines the helical blister has a thickness of between 0.001 and 0.003 cm but most preferably is 0.00254 cm thick. The helical band 62 segment on the other hand has a thickness of between approximately 0.006 and 0.012 cm but most preferably is 0.010 cm thick. The balloon member 16 is inflated during angioplasty via inflation outlet ports at the appropriate ranges of inflation pressure. The additional thickness of band 62 prevents it from expanding as much as the thin-walled balloon member 16 causing depression 66 to form, as depicted in FIG. 7. Depression 66 extends helically along the longitudinal axis of balloon member 14 and is designed to allow the maximum amount of blood to flow freely around balloon catheter 10 to the distal side of the stenosis and to side branching arteries. As an alternative to varying the thickness to create the integral helical band, the material of the balloon member 16 may be treated to reduce the elasticity of helical segment(s) thereof, or the balloon member may be welded or adhesively secured to the tubular member 14 to produce the desired groove configuration.

FIG. 8 depicts a fourth embodiment of the present invention, which is similar to the embodiment of FIG. 6 except that a double helix integral band 68 configuration is provided, again preferably by appropriately varying the thickness of the balloon member 16. When balloon member is inflated during surgery via suitably disposed inflation outlet ports the helical configuration of the integral bands 68 causes balloon member 16 to form balloon blisters 70, 72, 74, 76, 78.

FIGS. 9 and 10 depict a fifth embodiment of the balloon catheter 10 in accordance with the present invention. In this embodiment radial 79 and longitudinal grooves 80 are defined with, preferably integrally defined, radial and longitudinal bands 82, 84. The resulting cusps or blisters 86 promote a flushing of the grooves 79, 80. Balloon member 16 is preferably thin-walled as in previous embodiments and made from any resilient, elastomeric, medical-grade material. When inflated, all elements of balloon member 16 expand forming cavity 88. Cavity 88 extends longitudinally of the balloon member 16. Cavity 88 allows balloon member 16 to remain detachedly free from tubular member 14 thus providing the convenience of having only one inflation outlet port (not shown) in balloon inflation lumen 90. If desired, of course, a plurality of inflation ports may be provided.

Figure 11:
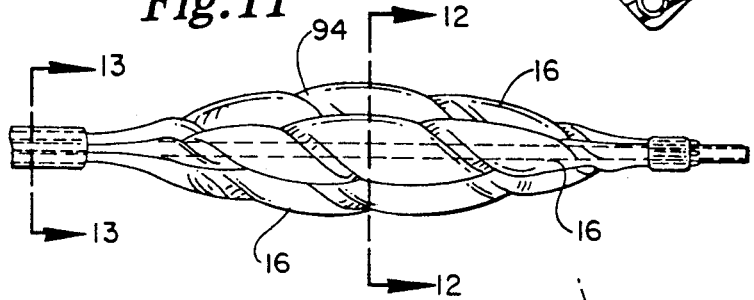
FIG. 11 is a side elevational view of a sixth embodiment of a balloon tip for a catheter in accordance with the present invention.

FIG. 11 depicts a sixth embodiment of the balloon catheter 10 in accordance with the present invention. In accordance with this embodiment, a plurality of balloon members 16 are provided, each having its own inflation lumen 92 incorporated in the catheter tubular member 14.

Each balloon member 16 has a helical groove 94 or alternatively, longitudinal and circumferential grooves defined therein, by thickness variation, material treatment, or by suitably forming the balloon member 16 from a memory material. Providing a plurality of tethered balloons ends permits additional passive perfusion in the gap(s) 96 between the tubular member 14 and the balloon members 16. More particularly, referring to FIG. 14, when inflated balloon members 16 form passive perfusion flow channels 96 and grooves 95. Grooves 95 create circumferential components of tension that are capable of maintaining larger passive perfusion flow channels 96 than those of prior art balloon catheters. These flow channels 96 allow the maximum amount of blood to flow from the proximal end of the balloon catheter 10 to the distal side of the occluded artery. As a further alternative, balloon members 16 may be tethered at various points along the cylindrical body creating additional grooves which provide for even greater passive perfusion space.

Figure 12:
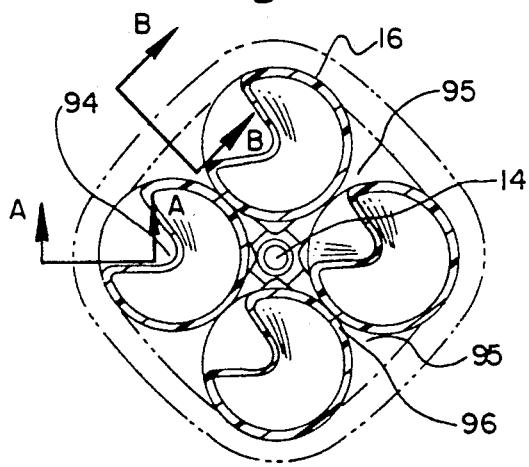
FIG. 12 is a cross-sectional view taken along line 12—12 of FIG. 11 depicting the stress on the inner layer of the arterial wall over the bridging region.
Figure 14:
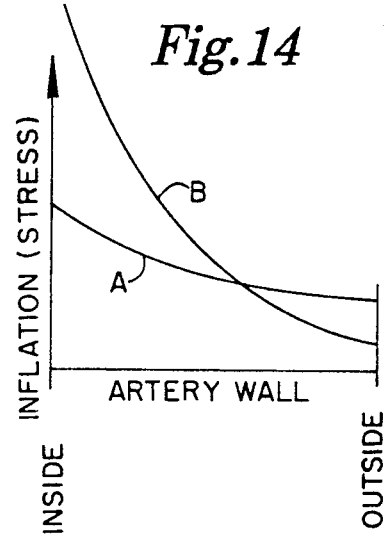
FIG. 14 is a graph illustrating inner and outer arterial wall stress caused by angioplasty balloon catheter inflation.
Figure 15:
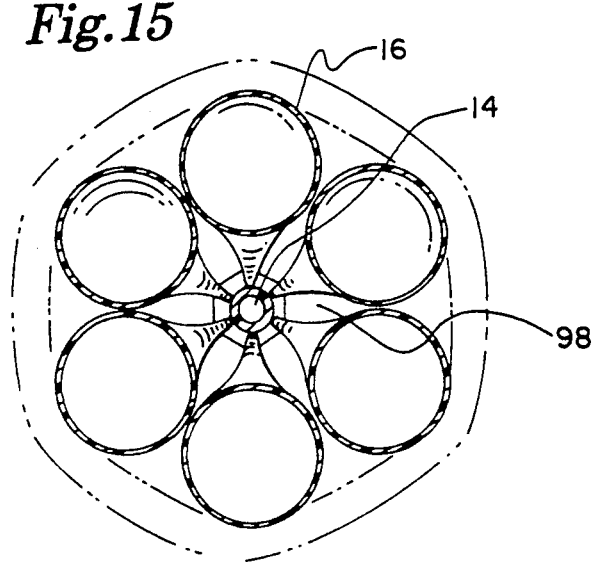
FIG. 15 is an enlarged fragmentary view of a seventh embodiment of a catheter in accordance with the present invention.

FIG. 12 shows an artery in phantom lines. When the balloon members 16 are inflated, the arterial wall expands creating varying degrees of stress on the expanded arterial wall. Because the strain on the inner layers of the artery wall is greater when the radius of curvature is greater, the artery wall stress distribution will produce a higher inner layer stress at the bridging position 13B than at the balloon position 13A, as can be seen in FIG. 14. In view of the foregoing, FIG. 15 depicts a modified form or seventh embodiment of a balloon catheter 10 in accordance with the present invention. The balloon catheter depicted in FIG. 15 is substantially similar to the balloon catheter depicted in FIGS. 11-12 except that the number of balloon members 16 has been increased from four to six creating additional blood flow channels 98. Grooves 94 may be defined in the surface of the balloon members 16 as in the embodiment of FIG. 11-12, although such is omitted from FIG. 15 for clarity. When balloon members 16 are inflated they exert outward radial forces around the circumference of the arterial wall causing the plaque to be compressed and displaced.

The above described embodiments of the invention may be used when performing known balloon angioplasty procedures and, therefore, a recounting of such known processes is unnecessary.

Figure 16A:
FIGS. 16a–16c are enlarged fragmentary views showing deployment of an eighth embodiment of a catheter in accordance with the present invention.
Figure 16B:
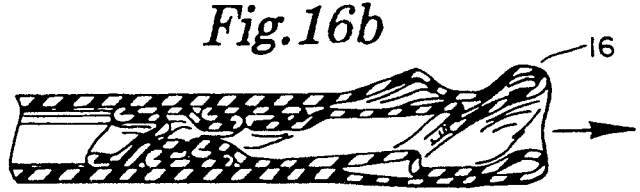
Figure 16C:
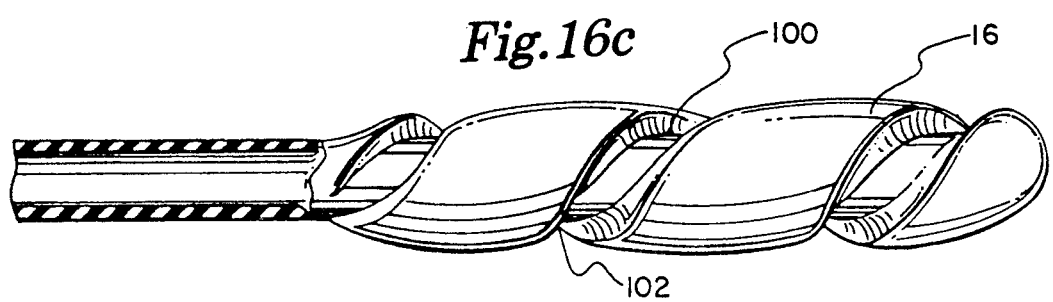

FIGS. 16a-16c depict a further modified form or eighth embodiment of a balloon catheter 10 in accordance with the present invention. In accordance with this embodiment, the balloon catheter is an everting catheter for use in dilation procedures in which a guide wire is not used. Thus, the lumen of the tubular member 14 stores the balloon member 16, inside out, prior to deployment. When the catheter 10 is in position and the dilation is to be commenced, inflation fluid is delivered under pressure through the lumen to gradually evert the balloon (FIG. 16b) until it reaches its fully deployed, and dilating, configuration (FIG. 16c). As shown in particular in FIG. 16c, the balloon member has integral groove(s) 100 defined in the wall of thereof thereby to define flow passages(s) 102 for blood and to minimize trauma to the body passage while still accomplishing the dilating function. Although a single groove 100 is shown in FIGS. 16a-16c, the employment of multiple helical and alternating longitudinal and circumferential grooves may also be employed in this embodiment.

Thus, the principal object of the invention is accomplished by employing single or multiple balloons which, at some range of inflation pressure (up to 10 atm), provide continuous open grooves from proximal to distal end of the balloon over which grooves the stressed artery wall bridges. The grooves are maintained open against the inflation pressure by virtue of circumferential components of wall tension. For an example of the need for circumferential tension, consider the following experiment: To a conventional angioplasty balloon of any size, including the smallest available size is added a single (or multiple) helical wrap of an elastomer having the property that when the balloon is inflated at some pressure equal to or less than the maximum allowed pressure, the elastomer wrap will create a helical (or double helical) path along which blood can flow past the balloon. Examples of such embodiments are shown in FIGS. 1 through 3. Such a balloon structure was constructed in the experiment described below. At modest pressures the balloon assumed the shape of FIGS. 1 through 3. As inflation pressure increased the groove cross-section progressed to the shape shown in FIG. 4, and with further inflation within a confining tube the groove closed down. This behavior represents the behavior of a grooved balloon in which the grooves close at elevated pressure and allow flow at intermediate pressure and represents one embodiment of the proposed invention.

Another proposed design modifies this behavior such that at elevated inflation pressures the groove is maintained open against the inner pressure by virtue of the distribution of the circumferential component of wall tension such that there is a circumferential component throughout the groove. One way of assuring this to be the case is to design the groove such that the wall is every where less steep than a radius originating from the balloon center. FIG. 5 shows a filled-vee shaped groove profile which satisfies this requirement while FIG. 4 cannot. Indeed, FIG. 4 depicts an unstable groove shape that will collapse when inflated because at high pressure, the side wall will close because there is no circumferential component of stress. The justification of the large radius of curvature of the top wall is that the artery wall which bridges the nearest lines of contact is under very high tension at elevated inflation pressures. The purpose of the groove is to provide as rich a blood supply as possible to the distal vasculature. The filled-vee shaped groove following the design constraints dictated by wall stability and shown in FIG. 5 is seen below to have an optimum flow if the half angle between the walls is 33 to 39 with the bottom of the vee filled as shown.

A further refinement of the basic invention is to select the incremental moduli of the heterogeneous balloon such that a change in inflation pressure can alter the depth of the indentation of the elastomeric wrap produced in the balloon surface. This modification represents another mechanism which would allow the balloon to have a full cylindrical shape at the high inflation pressures which are typically required to open a stenotic artery, a helically or otherwise indented shape permitting the passage of blood at the low to moderate inflation pressures which are typically used in the management of arterial dissection, and a completely deflated profile under negative pressure.

Thus, at very high pressures, no autoperfusion would occur, but at intermediate inflation pressures, the reformation of the indentation would lead to resumption of passive coronary perfusion.

In general, flow resistance considerations show that a single large groove, such as that depicted in FIGS. 1 and 3, provide greater blood flow than multiple smaller grooves which together offer the same total area of blood flow. However, the multiple blister or grooved embodiments (all of which are stabilized by a circumferential component of membrane tension) offer more endothelial reseeding sites, provide greater access to side branching arteries, should better forgive the occasional soft fatty blockage and provide shorter oxygen diffusion paths than the single grooved design. Examples are shown in FIGS. 8-10. A single balloon can tolerate at least 3 full sized grooves of optimum shape. In each case in the example shown, the groove is designed to be stable at elevated inflation pressures and have optimum hydraulic conductivity. In general the groove is designed to be stable at intermediate inflation pressures, open or closed at elevated pressures. The balloon catheters of the invention may be deployed in angioplasty, valvoplasty or other uses where passive perfusion is desired as single or multiple grooved balloons mounted on guide-wires, directly, on the outside of hollow catheters or inside hollow catheters to be evaginated through blockages and in each case make meaningful passive perfusion possible in procedures where it is not presently possible. For example, the grooved balloon applied to the Fogerty-Chin extrusion balloon (FIG. 16) transforms it into a passive perfusion balloon for treating total occlusions.

Irrespective of the configuration, an inflated balloon will block at least part of the artery cross-section and impede the flow. Hereinbelow, a mechanism of calculating the resistance to flow beyond the point of the arterial blockage will be detailed, based on the unblocked artery diameter at the point of blockage, the relative amount of resistance change the passive perfusion device introduces and then, rate that device as to its efficacy, c. Efficacy, c is defined as the flow expected with the balloon inflated in place divided by the flow expected if the artery were unobstructed.

The known autoperfusion catheter described on page 5 is designed to provide a flow of 60 to 70 ml/min at 80 mmHg pressure differential. In the considerations below, this resistance would permit approximately 50 percent of the flow expected in a 3 mm diameter artery supplying a distal resistance.

Thus, in a 3 mm artery, the efficacy of the known catheter is $c \approx 0.50$. The experience with the known catheter is good and suggests that the smaller beds supplied by smaller branch arteries which the present balloon design makes accessible would also benefit from an efficacy of approximately 0.50.

Estimating the Change in Resistance to Blood Flow

The normal flow through an unblocked artery can be estimated from Murray's Law which states that each generation of vasculature maintains the same wall shear stress. In human arteries this stress, $\tau$ ranges from 1.0 to 1.5 Pa. For design purposes, we assume:

$$\tau = 1.5 Pa \quad (1)$$

The relationship of arterial velocity, $U_a$, and unblocked artery diameter, $d_a$, is estimated by assuming the flow to be fully developed flow in a Newtonian fluid of viscosity, $$\mu = 0.003 kg/ms, \quad (2)$$

for which $$\tau = \mu \frac{8 U_a}{d_a} \quad (3)$$

Or inserting (1) and (2) in (3) and rearranging $$U_a = \frac{1.5 * d_a}{8 * 0.003} \approx 60 * d_a \, m/s \quad (4)$$

Experience with the known catheter suggests that a fraction of this flow, say, c, will permit prolonged balloon inflation. Then, if the hydraulic diameter of the passage on the outside of the balloon is $d_b$, the velocity through this passage, $U_b$ will be $$U_b = \frac{c U_a d_a^2}{d_b^2} = \frac{60 c d_a^3}{d_b^2} \quad (5)$$

where the hydraulic diameter is defined by $$d_b = \frac{4 * area}{perimeter} \quad (6)$$

where "area" is the area of the artery minus the area of the balloon and "perimeter" is measured around the opening between balloon and artery wall.

The Reynolds Number for flow through the balloon passage is $$\frac{U_b d_b \rho}{\mu} = \frac{60 c \rho d_a^3}{\mu d_b} = 2 * 10^7 * \frac{c d_a^3}{d_b} \quad (7)$$

where $\rho$ = blood density $\approx$ 1000 kg/m$^3$.

Pressure drop across the balloon passage, pb, is given by $$\Delta p_b = \frac{1}{2} \rho U_b^2 \left( K + 4 f_b \frac{L_b}{d_b} \right) \quad (8)$$

Here K is an entrance effect, is of order unity and is usually small compared to the second term and will be ignored here. $f_b$ is the friction factor for the balloon passage and $L_b$ the length of the balloon passage.

$$f_b = f_{bs} \frac{f_b}{f_{bs}} \quad (9)$$

Here $f_{bs}$ is the friction factor for a straight tube having the dimensions of the balloon passage and $f_b/f_{bs}$ is the ratio of the friction factor of a coiled passage to a straight passage. For laminar flow in a circular duct, fRe = 16. For laminar flow in a non-circular duct $10 < f_{bs} Re < 16$, say, $$f_{bs}Re = 13.25 \tag{10}$$

for the shapes of interest, it is known that $f_b/f_{bs}$ is estimated from $$\frac{f_b}{f_{bs}} = \frac{21.5 * Re\sqrt{\frac{d_b}{D_c}}}{\left(1.56 + \log_{10}Re\sqrt{\frac{d_b}{D_c}}\right)^{5.73}} \tag{11}$$

where $D_c$ is the diameter of the coil. $f_b/f_{bs}$ is found to be $1 < f_b/f_{bs} < 2$ in the calculation below. In addition, models of the groove for which $1 < D_c/d_a < 3$ give coil length $L_c = 1.2L$.

Efficacy for a Single Helical Groove

Recall that for $K=O$, equation (8) becomes $$\Delta p_b = \frac{1}{2} \rho U_b^2 4 f_b \frac{L_b}{d_b} \tag{8}$$

The $\Delta pb$ across the balloon represents the fraction of the systemic pressure drop, said $\Delta p = 10000$Pa which is unavailable to overcome the resistance of the vascular bed distal to the balloon. Assuming that the resistance proximal to the balloon is negligible compared to that distal to the balloon, then, if the flow is c*(the unrestricted flow, $Q_u$) i.e. $Q = cQ_u$, the pressure drop across the balloon is $$\Delta p_b = 10000(1-c) \text{ Pa} \tag{12}$$

Recall that the velocity is $$U_b = \frac{cU_a d_a^2}{d_b^2} = \frac{60 c d_a^3}{d_b^2} \tag{5}$$

$$f_{bs} = \frac{13.25}{2 * 10^7 * \frac{cd_a^3}{d_b}} \tag{13}$$

$L_b/d_b$ is estimated in the following way. The length of an angioplasty balloon is usually $10*d_a$. At a pitch of $\pi d_a/2$ along the balloon for each complete turn, the length becomes, $L_b = 1.2L$. Thus $$\frac{4L_b}{d_b} = \frac{50 d_a}{d_b} \tag{14}$$

Then $$\Delta p_b = 10000(1-c) = \frac{1}{2} \rho U_b^2 4 f_b \frac{L_b}{d_b} = \tag{15}$$

$$\frac{1}{2} \rho \left(\frac{60 c d_a^3}{d_b^2}\right)^2 \frac{13.25}{2 * 10^7 * \frac{cd_a^3}{d_b}} \frac{50 d_a f_b}{d_b f_{bs}}$$

Then with $\rho = 1000$ kg/m³

$$(1-c) = 0.006 c \left(\frac{d_a}{d_b}\right)^4 \frac{f_b}{f_{bs}} \tag{16}$$

or solving for c, $$c = \frac{1}{1 + 0.006 \left(\frac{d_a}{d_b}\right)^4 \frac{f_b}{f_{ba}}} \tag{17}$$

In order for $c = 0.5$ with $f_b f_{bs} \approx 1.4$, $d_a/d_b \approx 3.33$.

With this approximate value we obtain a first estimate of $f_b/f_{bs}$ from equation (1).

$$\frac{f_b}{f_{bg}} = \frac{21.5 * Re\sqrt{\frac{d_b}{D_c}}}{\left(1.56 + \log_{10}Re\sqrt{\frac{d_b}{D_c}}\right)^{5.73}} \tag{11}$$

$$d_b = 0.3 d_a, D_c = 2 d_a, \text{ say } \sqrt{\frac{d_b}{D_c}} =$$

$$0.378, \text{ and } Re = 8.33 * 10^6 d_a^2$$

Then with $d_b = 0.2 d_a$, and $c = 0.5$, (11) becomes $$\frac{f_b}{f_{bs}} = \frac{21.5 * 2.5 * 10^7 d_a^2/3}{(1.56 + \log_{10} 2.5 * 10^7 d_a^2/3)^{5.73}} = \tag{11}$$

$$\frac{1.8 * 19^8 d_a^2}{(1.56 + \log_{10} 8.33 * 10^6 d_a^2)^{5.73}}$$

Figure 17:
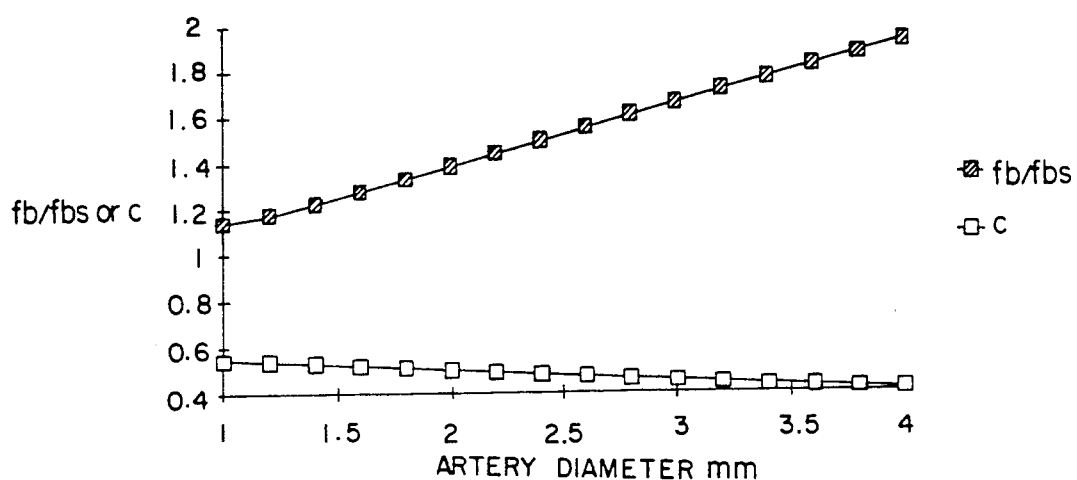
FIG. 17 is a graph of $f_b/f_{bs}$, c vs. Artery Diameter.
Figure 18:
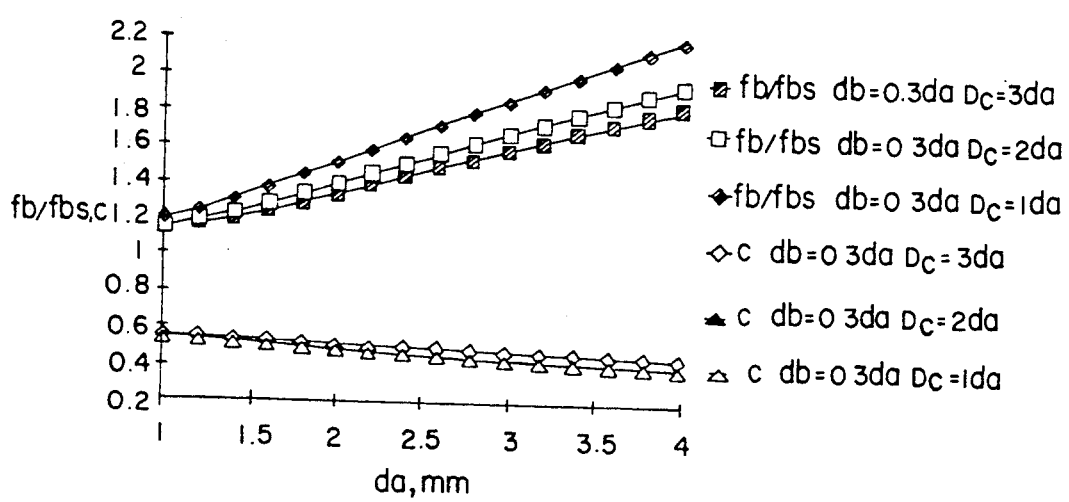
FIG. 18 is a graph of $f_b/f_{bs}$, c vs. da.

With this first approximation of $f_b/f_{bs}$ a new estimate of Re and c are obtained, and a second estimate of $f_b/f_{bs}$ made and so on until the $f_b/f_{bs}$ does not change with successive iterations. FIG. 17 gives the behavior of $f_b/f_{bs}$ and c vs $d_a$ for $d_b/d_a = 0.3$ and $D_c = 2d_a$. FIG. 18 shows the influence of coil diameter, $D_c$ on $f_b/f_{bs}$ and c. It can be seen that the influence on c is not a strong one.

Some representative results are:

For $d_a = 0.003$ m, $f_b/f_{bs} 1.66$ and $c = 0.449$;
For $d_a = 0.002$ m, $f_b/f_{bs} 1.27$ and $c = 0.516$;
For $d_a = 0.001$ m, $f_b/f_{bs} 1.14$ and $c = 0.544$.

We see that for single grooves in single balloons, if $d_b \approx 0.3 d_a$, $c \approx 0.5$. These smaller balloons are as efficacious as the known catheter is for a 3 mm artery and offer the advantage that the balloons can be used in smaller arteries. As shown below, the optimum groove occupies approximately 1/6 of the balloon perimeter and produces flow equivalent to the known catheter which has been found efficacious for large arteries. If more flow is needed, a single balloon could accommodate up to 3 groves. Multiple grooves in a single balloon should produce efficacies given by $$c = \frac{1}{1 + \frac{0.006}{n} \left(\frac{d_a}{d_b}\right)^4 \frac{f_b}{f_{bg}}} \tag{17'}$$

For the embodiment shown in FIG. 9, $f_b/f_{bs} \approx 1$, $n = 3$, $d_a/d_b 3.33$ so that $c = 0.8$.

Hydraulic Diameters

At Intermediate Inflation Pressure

At intermediate inflation pressures the distribution of the circumferential component of wall tension can be limited to the groove base generating the shape of groove discussed in the next two sections. The hydraulic diameter is 4* the cross sectional area (region 104 in FIG. (4)) divided by the perimeter.

A Single Helical Passage

In order to achieve a c=0.5, $d_b/d_a 32 > 0.30$. Consider the passage 104 shown in FIG. 4. Let the radius of the passage at the base be r, that of the two shoulders at the top be ar, where a is a constant, and a straight segment connecting the two arcs of length br. The arterial wall will tend to be straight at high inflation pressures. Then the area will be $$\text{area} = (2ar + 2r) \times ar - \frac{\pi (ar)^2}{2} + \frac{\pi r^2}{2} + 2rbr \qquad (18)$$

and the $$\text{perimeter} = \pi r + 2br + \pi ar + (2a+2)r \qquad (19)$$

Then the hydraulic diameter is $$d_b = 4 \times \frac{(2ar + 2r) \times ar - \frac{\pi (ar)^2}{2} + \frac{\pi r^2}{2} + 2rbr}{\pi r + 2br + \pi ar + (2a+2)r} \qquad (20)$$

Sample results, a=1

| b | $d_b/2r$ |
|---|---|
| 0 | 0.778 |
| ·1 | 0.977 |
| 3 | 1.12 |

Suppose a=2,

| b | $d_b/2r$ |
|---|---|
| 0 | 0.945 |

Thus the hydraulic diameter is very nearly equal the width of the passage which constitutes the helical groove in the balloon. From the above $d_b/d_a \approx .3$ requires $2r/d_a \approx 0.3$.

Multiple Balloons

With n balloons producing n flow passages of hydraulic diameter, $d_b$ and length=$10d_a$ the efficacy, c, can be shown to be $$c = \frac{1}{1 + \frac{0.005}{n}\left(\frac{d_a}{d_b}\right)^4}$$

with straight cylindrical balloons and $$c = \frac{1}{1 + \frac{0.0055}{n}\left(\frac{d_a}{d_{bhg}}\right)^4}$$

with helical grooves in each balloon.

This flow passage is estimated by assuming the balloons inflate to circular cross sections and the taught artery wall is stretched straight between adjacent balloons. The catheter is assumed to be vanishingly small. Then if each balloon has a diameter, $d_n$, then $$d_b = d_n * \frac{4 \cdot \pi}{\pi + 2} = 0.167 d_n \qquad (18)$$

With helical grooves we ignore the inner volumes and estimate $$d_{bhg} = 4 * d_n * \frac{1 - \pi/4 + 2\pi/9}{2\pi/3 + 2 + 3\pi/4 + 2/3} = 0.2455 d_n \qquad (19)$$

n balloons of diameter $d_n$ produce a stretched artery of diameter, $$d_a = d_n \frac{\pi + n}{\pi} \qquad (20)$$

| n | $d_n/d_a$ | $d_b/d_a$ | c | $d_{bhg}/d_a$ | $c_{hg}$ |
|---|---|---|---|---|---|
| 2 | 0.611 | 0.102 | 0.041 | 0.15 | 0.1555 |
| 3 | 0.5115 | 0.0853 | 0.031 | 0.1256 | 0.1195 |
| 4 | 0.440 | 0.0735 | 0.023 | 0.1080 | 0.0900 |
| 5 | 0.386 | 0.0645 | 0.017 | 0.095 | 0.0689 |
| 6 | 0.344 | 0.0575 | 0.013 | 0.084 | 0.0526 |

Thus, for the best multiple balloon configuration without helical grooves the highest fraction of blood flow allowed is 1/8 the single helical groove value. Multiple balloons with helical grooves show efficacies nearly 4 times as high. If these balloons each had 2 to 3 grooves the effect would be better still. If the obstruction restricted the flow for only part of the balloon length the efficacy would be higher. For example, if n=2 and the obstruction one half the balloon length, $c_{hg}$=0.2957. Since these designs will offer more reseeding sites, more access to side branches and shorter $O_2$ diffusion paths than single balloons the reduced c may be compensated for by better long range outcome.

At High Inflation Pressures

At elevated inflation pressures the distribution of forces can cause the top of the grooves to close with an accompanying reduction of hydraulic diameter. To prevent this from happening the grooves are designed so that in cross section, the slope of the wall at a point on the surface is every where greater than the slope of a radius at that point. For example, the grooves shown in FIG. 5 satisfy this requirement, while the groove of FIG. 4 does not.

To estimate the included angle which provides the highest potential hydraulic diameter, consider the model of a groove consisting of an equilateral triangle in which the two equal sides represent balloon walls and the top represents the taught artery wall. The length of the side walls must be slightly less than the radius of the inflated artery, $d_a/2$, say, r. The half angle between the side walls is $\Theta$.

The area of the groove is $$\text{Area} = (1.2) 2r \sin \Theta * r \cos \Theta \qquad (21)$$

The perimeter is $$\text{perimeter} = 2r + 2r \sin \Theta \qquad (22)$$

The hydraulic diameter, $d_b$ 4*area/perimeter, is $$d_b = 2r \frac{\sin\theta \cos\theta}{1 + \sin\theta} \qquad (23)$$

This is found to have a maximum at $\Theta = 38$ degrees at which $$\frac{\sin\theta\cos\theta}{1 + \sin\theta} = 0.3003.$$

Figure 19:
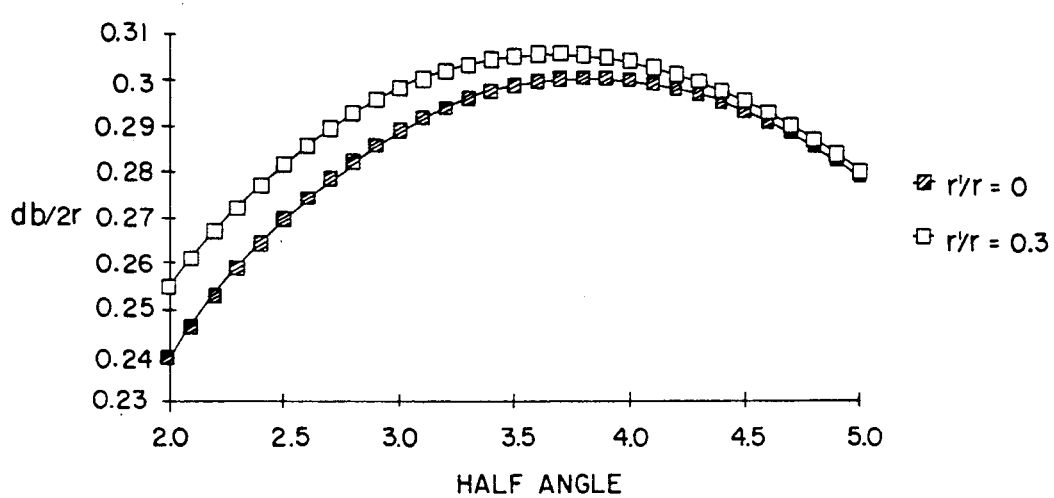
FIG. 19 is a graph of $d_b/2r$ vs. half angle.
Figure 20:
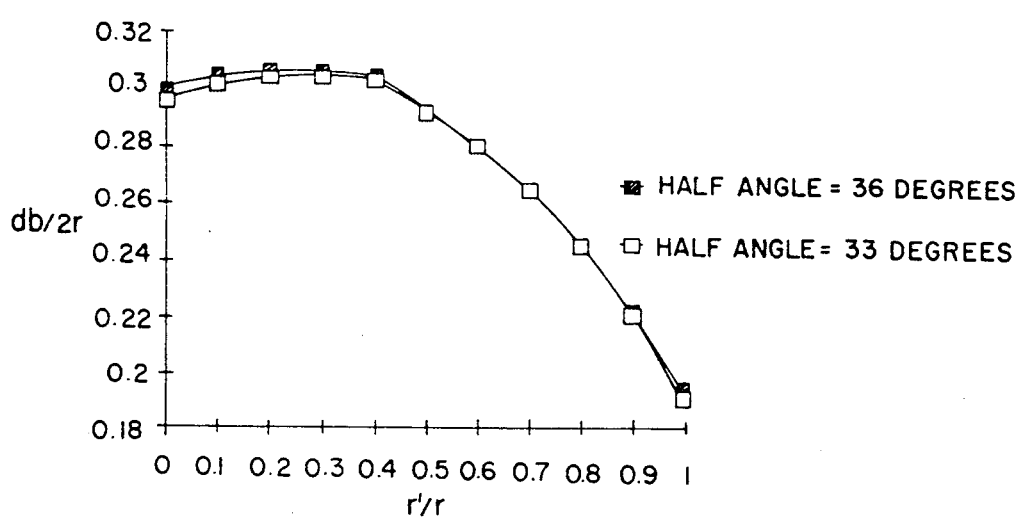
FIG. 20 is a graph of $d_b/2r$ vs. r'/r.

The filled vee shape is modeled by supposing there is a radius r'' supplanting the sharp vee, tangent to the side wall at a position r' from the apex of the vee. Then the hydraulic diameter as a function of $\Theta$ for two values of r' is as shown in FIG. 19. For a fixed $\Theta$ the radius of the filling groove also yields a maximum shown in FIG. 20. When both are varied there is also an extemum in the $d_b$ vs $\Theta$ and r'' plane giving the local maximum. Here it is found that the maximum occurs at a half angle of 37 degrees and an r'/r=0.3. $d_b/2r=0.3054$; in order for $d_b/d_a$ to be 0.3, $2r/d_a=0.98$. The filled-vee groove offering stability against high pressure and giving optimum $d_b$ is shown in FIG. 5.

At high balloon inflation pressures the groove radius at the intersection of balloon and artery is expected to be relatively small so that the model is representative at that site. It is expected that to ensure space for the catheter or guide wire the apex of the groove would have the point of tangency of the radius r'' to be at an r'/r>0.3. Then for a single groove $d_b/2r$ would be less than 0.3 and as a result c would be less than 0.5. This difficulty can be overcome by having multiple grooves. If $$c = \frac{1}{1 + x}$$

and $x>1$, $c<1$. For example suppose a small single groove produces an $x=1.2$, $c=0.454$. If n grooves of the same $d_b$ are in the balloon, $$c = \frac{1}{1 + x/n};$$

if $n=2$, $c=0.625$; if $n=3$, $c=0.714$.

Although descriptions of the preferred embodiments have been presented, it is contemplated that various changes, including those mentioned above, could be made without deviating from the spirit of the present invention. For example, although the invention has been described with reference to dilating stenosed blood vessels, the principles of the invention could be applied to the dilation of other body ducts, such as, for example, ureters to dilate the same while minimizing trauma to the duct wall and while allowing the passage of urine. It is therefore desired that the present embodiment be considered in all respects as illustrative, not restrictive, and that reference be made to the appended claims rather than to the foregoing description to indicate the scope of the invention.

What is claimed is:

1. A passive perfusion angioplasty catheter comprising:
    an elongated flexible member defining an inflation lumen; and
    inflatable balloon means affixed to a distal end of said flexible member for pressing against an interior surface of an arterial lumen, said balloon means defining at least one passage between an exterior thereof and said interior surface of said arterial lumen for permitting blood to flow past said balloon means when said balloon means is pressed against said interior surface,
    said balloon means comprising at least one inflatable lobe, said at least one passage being a helical groove defined by said at least one lobe, a band being helically wound about a longitudinal axis of said balloon means, ends of said band being affixed to said flexible member, thereby defining a helical lobe and said helical groove.

2. The catheter claimed in claim 1, wherein said band is affixed to said flexible member by distal and proximal wraps.

3. The catheter claimed in claim 1, wherein said balloon means is made from one of polyvinyl chloride, polyethylene, polyethylene terephthalate and polyolefin copolymer.

4. The catheter claimed in claim 1, wherein said flexible member further includes a guide wire lumen one of coaxial with and adjacent to said inflation lumen.

5. The catheter claimed in claim 1, wherein said inflation lumen further includes a plurality of inflation ports for inflating said balloon means.

6. The catheter claimed in claim 1, wherein said balloon means comprises a single balloon member disposed in surrounding relation to said flexible member.

7. The catheter claimed in claim 1, wherein said balloon means comprises a plurality of balloon members disposed in an array about said flexible member, said flexible member having a plurality of inflation lumens, each said balloon member being operatively coupled to one of said plurality of inflation lumens.

8. A passive perfusion angioplasty catheter comprising:
    an elongated flexible member defining an inflation lumen; and
    inflatable balloon means affixed to a distal end of said flexible member for pressing against an interior surface of an arterial lumen, said balloon means defining at least one passage between an exterior thereof and said interior surface of said arterial lumen for permitting blood to flow past said balloon means when said balloon means is pressed against said interior surface, said balloon means including a plurality of lobes defining first and second helical passages.

9. The catheter as claimed in claim 8, wherein said helical passages are defined by winding first and second bands helically about said balloon means, said first band being wound helically clockwise about a longitudinal axis of said balloon means, said second band being wound helically counterclockwise about the longitudinal axis of said balloon means, ends of said first and second bands being affixed to said flexible member, said first and second bands also defining said plurality of lobes.

10. The catheter as claimed in claim 9, wherein said bands are affixed to said flexible member by distal and proximal wraps.

11. The catheter as claimed in claim 2 or 10, wherein said wraps are made from one of polyethylene terephthalate and polyolefin copolymer.

12. The catheter as claimed in claim 8, wherein said balloon means is made from one of polyvinyl chloride, polyethylene, polyethylene terephthalate and polyolefin copolymer.

13. The catheter as claimed in claim 8, wherein said flexible member further includes a guide wire lumen one of coaxial with and adjacent to said inflation lumen.

14. The catheter as claimed in claim 8, wherein said inflation lumen further includes a plurality of inflation ports for inflating said balloon means.

15. The catheter as claimed in claim 8, wherein said balloon means comprises a single balloon member disposed in surrounding relation to said flexible member.

16. The catheter as claimed in claim 8, wherein said balloon means comprises a plurality of balloon members disposed in an array about said flexible member, said flexible member having a plurality of inflation lumens, each said balloon member being operatively coupled to one of said plurality of inflation lumens.

17. A passive perfusion angioplasty catheter comprising:
   an elongated flexible member defining an inflation lumen; and
   inflatable balloon means affixed to a distal end of said flexible member for pressing against an interior surface of an arterial lumen, said balloon means defining at least one passage between an exterior thereof and said interior surface of said arterial lumen for permitting blood to flow past said balloon means when said balloon means is pressed against said interior surface,
   said balloon means comprising at least one inflatable lobe, said at least one passage being a helical groove defined by said at least one lobe, said balloon means comprises at least one inflatable lobe portion, said inflatable lobe portion being formed so as to have a material thickness less than remaining portions thereof, whereby during inflation of said balloon means, lobe portions distent to a greater extent than said remaining portions.

18. The catheter as claimed in claim 17, wherein a portion of said balloon means defining said at least one passage has a thickness between 0.006 and 0.012 cm and a portion of said balloon means defining said lobes has a thickness between 0.001 and 0.003 cm, whereby said passage portion expanding less than said lobe portion upon inflation of said balloon means.

19. The catheter as claimed in claim 17, wherein said flexible member further includes a guide wire lumen one of coaxial with and adjacent to said inflation lumen.

20. The catheter as claimed in claim 17, wherein said inflation lumen further includes a plurality of inflation ports for inflating said balloon means.

21. The catheter as claimed in claim 17, wherein said balloon means comprises a single balloon member disposed in surrounding relation to said flexible member.

22. The catheter as claimed in claim 17, wherein said balloon means comprises a plurality of balloon members disposed in an array about said flexible member, said flexible member having a plurality of inflation lumens, each said balloon member being operatively coupled to one of said plurality of inflation lumens.

23. A passive perfusion angioplasty catheter comprising:
   an elongated flexible member defining an inflation lumen; and
   inflatable balloon means affixed to a distal end of said flexible member for pressing against an interior surface of an arterial lumen, said balloon means defining at least one passage between an exterior thereof and said interior surface of said arterial lumen for permitting blood to flow past said balloon means when said balloon means is pressed against said interior surface,
   said balloon means including a plurality of S-shaped pleats defined in the periphery thereof when said balloon means is in a relaxed state, each said pleat having a radius of curvature of 2.5 to 5 times a thickness of the balloon means material.

24. The catheter as claimed in claim 23, wherein said pleats have a height of $4r_c + \delta$ in said relaxed state,
   where $r_c$ is the radius of curvature of said pleat,
   and $\delta$ is the thickness of said pleat.

25. The catheter as claimed in claim 23, wherein said flexible member further includes a guide wire lumen one of coaxial with and adjacent to said inflation lumen.

26. The catheter as claimed in claim 23, wherein said inflation lumen further includes a plurality of inflation ports for inflating said balloon means.

27. The catheter as claimed in claim 23, wherein said balloon means comprises a single balloon member disposed in surrounding relation to said flexible member.

28. The catheter as claimed in claim 23, wherein said balloon means comprises a plurality of balloon members disposed in an array about said flexible member, said flexible member having a plurality of inflation lumens, each said balloon member being operatively coupled to one of said plurality of inflation lumens.

29. A passive perfusion angioplasty catheter comprising:
   an elongated flexible member defining an inflation lumen;
   inflatable balloon means affixed to a distal end of said flexible member for pressing against an interior surface of an arterial lumen, said balloon means defining a plurality of passages between an exterior thereof and said interior surface of said arterial lumen for permitting blood to flow past said balloon means when said balloon means is pressed against said interior surface, at least some of said passages being defined longitudinally and at least some of said passages being defined circumferentially, of said balloon means; and
   means defining a cavity, said cavity extending longitudinally of said balloon means and being disposed between said balloon means and said flexible member.

30. The catheter as claimed in claim 29, wherein said flexible member further includes a guide wire lumen one of coaxial with and adjacent to said inflation lumen.

31. The catheter as claimed in claim 29, wherein said inflation lumen further includes a plurality of inflation ports for inflating said balloon means.

32. The catheter as claimed in claim 29, wherein said balloon means comprises a single balloon member disposed in surrounding relation to said flexible member.

33. The catheter as claimed in claim 29, wherein said balloon means comprises a plurality of balloon members disposed in an array about said flexible member, said flexible member having a plurality of inflation lumens, each said balloon member being operatively coupled to one of said plurality of inflation lumens.

34. A passive perfusion angioplasty catheter comprising:
   an elongated flexible member having one of a core tube and cylinder and a concentric tube defining an inflation lumen; and
   inflatable balloon means, the distal end of which being affixed to the core tube while the proximal end is sealed to the concentric tube such that an interior of the balloon means being a continuation of the inflation lumen, the formed shape consisting of a pleated cylindrical balloon in which the pleats have a radius $r_c$ and the polymer has a thickness, $\delta$, and, as cast, the pleated balloon will, when collapsed onto a surface of the core tube of said flexible member give a deflated profile $4r_c + \delta$ greater than a radius of said core tube of said flexible member, and when fully inflated will produce a smooth unpleated balloon surface with surface area approximately that of the cast pleated area.

35. A catheter as in claim 34, wherein depending on the polymer chosen, the ratio $r_c/\delta$ is such that yield strain of the polymer is not exceeded when the pleat is flexed from fully pleated to fully open or unpleated, with $2 < r_c/\delta < 5$.

36. A catheter as in claim 34, wherein the pleats are sufficient to prevent formation of wings which exist in a deflated unpleated balloon.

37. A catheter as claimed in claim 34 wherein the deflated pleated balloon is wrapped by a confining at least one elastomeric band such that when the balloon is inflated to an intermediate pressure, single or multiple helical grooves are formed allowing passage for blood flow while distending artery walls.

38. A catheter as claimed in claim 37, wherein said at least one elastomeric band is made to stretch with further inflation pressure allowing the balloon to exert a higher distending pressure to the artery momentarily while maintaining diminishing passive perfusion until full inflation is reached, reduction in pressure restoring the flow passage while maintaining distending pressure.

39. A catheter as claimed in claim 34, wherein the deflated pleated balloon is wrapped by confining at least one axial elastomeric band such that when the balloon is inflated to an intermediate pressure, single or multiple axial grooves are formed by restraining said axial elastomeric band at axial intervals by radial elastomeric bands allowing passage for blood flow while distending artery walls.

40. A catheter as claimed in claim 39 wherein said at least one elastomeric band is made to stretch with further inflation pressure allowing the balloon to exert a higher distending pressure to the artery momentarily while maintaining diminishing passive perfusion until full inflation is reached, reduction in pressure restoring the flow passage while maintaining distending pressure.

41. A passive perfusion angioplasty catheter comprising:
an elongated flexible member having one of a core tube and cylinder and a concentric tube defining an inflation lumen; and
inflatable balloon means, the distal end of which being affixed to the core tube while the proximal end is sealed to the concentric tube such that an interior of the balloon means being a continuation of the inflation lumen, said balloon means distending the surrounding arterial walls while allowing an open passage to remain between a distended artery wall and one of a depressed groove and set of grooves formed by the balloon means allowing blood to flow past a surface of the balloon means, said balloon means being fabricated from a polymer having an elastic modulus substantially greater than arterial tissue and is thermally pressure formed to assume a desired shape upon inflation, the formed shape consisting of a partially pleated balloon in which the pleats have a radius $r_c$ and the polymer a thickness, $\delta$, as cast the pleated balloon will, when collapsed onto a surface of the interior tube of said flexible member give a deflated profile $4r_c + \delta$ greater than a radius of said core tube of said flexible member, and when fully inflated will produce an unpleated balloon surface with surface area approximately that of the cast pleated area and with single or multiple grooves formed by the unpleated, undistended portion of a polymeric tube from which the balloon is blown.

42. A catheter as claimed in claim 41, wherein the grooves are assured against collapse as inflation pressure is increased by having side walls whose tangents pass on a near side of the catheter centerline and a radial component of stress is maintained by intermittent bands for axial grooves or by adequate pitch when helical grooves are employed.

43. A catheter as claimed in claim 42, wherein the grooves provide an optimum shape for delivering blood from one side of the balloon to the other, each groove wall has a single tangent and said tangent passes substantially through the catheter centerline, said optimum shape in a filled wedge with a half angle of $37° \pm 2°$.

44. A catheter as claimed in claim 42, wherein the grooves provide an optimum shaped passage for delivering blood from one side of the balloon to the other, said optimum shape being defined for any distribution of side wall slope as the shape providing a maximum hydraulic diameter for the passage bounded by the bottom and side walls of the balloon groove on each side and capped by a taut artery wall on top, said hydraulic diameter being defined as four times the passage cross sectional area divided by the passage perimeter.

45. A passive perfusion angioplasty catheter comprising:
an elongated flexible member having one of a core tube and cylinder and a concentric tube defining an inflation lumen; and
a manifold connecting inflatable grooved balloon means, distal ends of which being affixed to the core tub while proximal ends thereof being sealed to the concentric tube by way of the manifold such that an interior of the balloon means is a continuation of the inflation lumen, said grooved balloon means distending surrounding arterial walls while allowing an open passage to remain between the distended artery wall and a depressed groove or set of grooves formed by the balloon means and valleys between the balloon means allowing blood to flow past the balloon means surface.

46. A catheter as claimed in claim 45, wherein the balloon means includes a plurality of balloons, each balloon having one of a single groove, two groves and three grooves disposed helically or axially with circumferential band pattern.

47. A catheter as claimed in claim 45, wherein the balloon means includes a plurality of balloons, the balloons being cast as pleated or unpleated elongated circular cylinders with the grooves formed by elastomeric wraps.

48. A catheter as claimed in claim 45, wherein the balloon means includes a plurality of balloons, the balloons being cast as pleated or unpleated elongated circular cylinders with the grooves formed during a blowing process.

49. A catheter as claimed in claim 45, wherein flow resistance for a summation of grooves is equal or less than flow resistance distal to an arterial treatment site.

50. A passive perfusion angioplasty catheter comprising:

an elongated flexible member having one of a core tube defining a lumen; and inflatable balloon means having one of a pleated and unpleated grooved balloon being blown into a mold thereof directly from the lumen, said balloon being sucked into the lumen and threaded to an occluded site where, upon being pressurized, the balloon evaginates forming a grooved balloon providing passive perfusion when opening tightly occluded vessels.

51. A passive perfusion angioplasty catheter as claimed in claim 50 wherein the grooves are assured against collapse as inflation pressure is increased by having side walls whose tangents pass on a near side of the catheter centerline and a radial component of stress is maintained by intermittent bands for axial grooves or by adequate pitch when helical grooves are employed.

52. A passive perfusion angioplasty catheter as claimed in claim 51 wherein the grooves provide an optimum shaped passage for delivering blood from one side of the balloon to the other, said optimum shape being defined for any distribution of side wall slope as the shape providing a maximum hydraulic diameter for the passage bounded by the bottom and side walls of the balloon groove on each side and capped by a taut artery wall on top, said hydraulic diameter being defined as four times the passage cross sectional area divided by the passage perimeter.

53. A method of percutaneous transluminal angioplasty comprising the steps of:

providing a catheter having an elongated flexible member defining an inflation lumen and inflatable balloon means affixed to a distal end of said flexible member for pressing against an interior surface of an arterial lumen, said balloon means defining at least one passage between an exterior thereof and said interior surface, said balloon means having a plurality of lobes defining first and second helical passages, said helical passages being defined by helically winding first and second bands about said balloon means, said first band being wound helically clockwise about a longitudinal axis of said balloon means, said second band being wound helically counterclockwise about the longitudinal axis of said balloon means, ends of said first and second bands being affixed to said flexible member, said first and second bands also defining said plurality of lobes;

inserting said catheter into an artery so that said balloon means is disposed at point were blood flow is restricted;

inflating and expanding said balloon means so that said balloon means presses against the interior surface of the arterial lumen to reduce a constriction in the artery; and permitting blood to flow in said at least one passage so as to flow past said balloon means.

54. The method as claimed in claim 53, wherein the step of providing a catheter includes providing said balloon means having a plurality of balloon members disposed in an array about said flexible member, said flexible member having a plurality of inflation lumens, each said balloon member being operatively coupled to one of said plurality of inflation lumens.

55. A method of percutaneous transluminal angioplasty comprising the steps of:

providing a catheter having an elongated flexible member defining an inflation lumen and inflatable balloon means affixed to a distal end of said flexible member for pressing against an interior surface of an arterial lumen, said balloon means defining at least one passage between an exterior thereof and said interior surface, said balloon means having at least one inflatable lobe, said at least one passage being a helical groove defined by said at least one lobe, a band being helically wound about a longitudinal axis of said balloon means, ends of said band being affixed to said flexible member, thereby defining a helical lobe and helical groove;

inserting said catheter into an artery so that said balloon means is disposed at point were blood flow is restricted;

inflating and expanding said balloon means so that said balloon means presses against the interior surface of the arterial lumen to reduce a constriction in the artery; and permitting blood to flow in said at least one passage so as to flow past said balloon means.

56. The method as claimed in claim 55, wherein the step of providing a catheter includes providing said balloon means having a plurality of balloon members disposed in an array about said flexible member, said flexible member having a plurality of inflation lumens, each said balloon member being operatively coupled to one of said plurality of inflation lumens.

* * * * *